United States Patent [19]

Schmid et al.

[11] Patent Number: 4,579,916

[45] Date of Patent: Apr. 1, 1986

[54] CURABLE MIXTURES CONTAINING AN EPOXIDE RESIN, AN IMIDE AND A CURING CATALYST

[75] Inventors: Rolf Schmid, Schwarzenburg; Alfred Renner, Muntelier; Werner Stauffer, Fribourg; Michael Fischer, Tafers, all of Switzerland

[73] Assignee: Ciba-Geigy Corporation, Ardsley, N.Y.

[21] Appl. No.: 669,414

[22] Filed: Nov. 8, 1984

[30] Foreign Application Priority Data

Nov. 15, 1983 [CH] Switzerland .................. 6137/83

[51] Int. Cl.$^4$ .................. C08G 59/44; C08G 59/46
[52] U.S. Cl. .................. 525/502; 525/530; 528/94; 528/97; 528/98; 528/99; 528/102; 528/117; 528/314; 528/322
[58] Field of Search .................. 528/117, 94, 97, 98, 528/99, 102, 314, 322; 525/530, 502

[56] References Cited

U.S. PATENT DOCUMENTS

| | | |
|---|---|---|
| 3,105,839 | 10/1963 | Renner . |
| 3,429,947 | 2/1969 | van Eygen .................. 528/117 |
| 3,651,012 | 3/1972 | Holub .................. 525/530 |
| 4,127,615 | 11/1978 | Zahir et al. . |
| 4,130,600 | 12/1978 | Zahir et al. . |
| 4,436,892 | 3/1984 | Zondler et al. . |
| 4,460,783 | 7/1984 | Nishikawa et al. . |
| 4,515,962 | 5/1985 | Renner . |

OTHER PUBLICATIONS

P. W. R. Beaumont et al., J. Materials Science, 10, 1334, (1975).
R. J. Young et al., J. Materials Science, 11, 776, (1979).

*Primary Examiner*—C. Warren Ivy
*Attorney, Agent, or Firm*—Luther A. R. Hall

[57] ABSTRACT

Heat-curable mixtures, containing (a) an epoxide resin having on average more than one epoxide group in the molecule, (b) an allyl-substituted or methallyl-substituted imide of the formula I

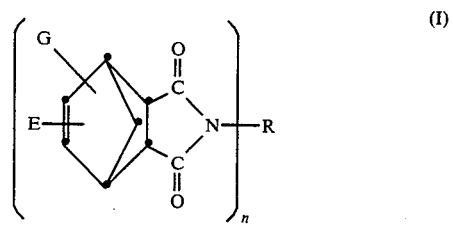

(I)

in which E is allyl or methallyl, G is hydrogen or methyl, n is 1 or 2, and R is hydrogen, alkyl, alkenyl, cycloalkyl, aryl, benzyl or arylene, and (c) a curing catalyst, have good storage stability and processability and produce moulded materials having high mechanical strength values and good resistance to heat.

11 Claims, No Drawings

CURABLE MIXTURES CONTAINING AN EPOXIDE RESIN, AN IMIDE AND A CURING CATALYST

The present invention relates to heat-curable mixtures containing an epoxide resin, an allyl-substituted or methallyl-substituted imide and a curing catalyst, and to the moulded materials, coatings or adhesive bonds obtained from these mixtures by curing.

Heat-curable mixtures of dimaleimides or polymaleimides, epoxide compounds containing at least one allyl group, and, if appropriate, curing agents for epoxide resins and/or curing accelerators are known from German Offenlegungsschrift No. 2,726,821. German Offenlegungsschrift No. 2,726,846 discloses heat-curable mixtures containing dimaleimides or polymaleimides, alkenylphenols and/or alkenylphenol ethers, epoxide compounds containing at least one alkyl group and, if appropriate, curing accelerators. These previously known curable mixtures are not without problems in regard to processing, since, in order to prepare homogeneous mixtures, it is necessary either to use an organic solvent or, if working in the absence of a solvent, to melt these mixtures at relatively high temperatures. In addition, the resistance to heat-ageing of the moulded materials prepared from these mixtures leaves something to be desired.

It has now been found that the disadvantages mentioned above can be avoided by using certain allyl-substituted or methallyl-substituted imides mixed with epoxide resins and curing catalysts.

The invention relates, therefore, to a heat-curable mixture which is stable on storage and contains (a) 5 to 95 parts by weight of an epoxide resin having on average more than one epoxide group in the molecule, (b) 95 to 5 parts by weight of an allyl-substituted or methallyl-substituted imide of the formula I

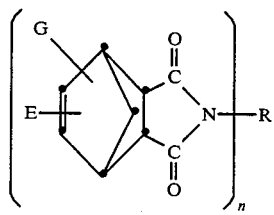

(I)

in which E is allyl or methallyl, G is hydrogen or methyl and n is 1 or 2 and, if n is 1, R is hydrogen, alkyl having 1–12 C atoms, alkenyl having 3–6 C atoms, cycloalkyl having 5–8 C atoms, aryl having 6–10 C atoms, such as phenyl, tolyl, xylyl, hydroxyphenyl or naphthyl, or benzyl or, if n is 2, R is $—C_mH_{2m}—$ in which $m=2–20$, arylene having 6–10 C atoms, such as m-phenylene, p-phenylene, 1,3-naphthylene, 1,4-naphthylene or 1,5-naphthylene, or a group of the formula II

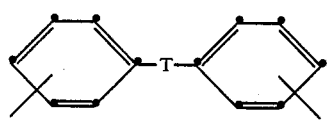

(II)

in which T is methylene, isopropylidene, CO, O, S or $SO_2$, and in which the total of (a) and (b) in the mixture is 100 parts by weight, and (c) 1 to 15 parts by weight, based on 100 parts by weight of the mixture of (a) and (b), of a curing catalyst.

In formula I, G is preferably a hydrogen atom.

The mixture according to the invention preferably contains 20 to 70 parts by weight, in particular 30 to 60 parts by weight, of the epoxide resin (a), 80–30 parts by weight, in particular 70 to 40 parts by weight, of the imide (b) and 3 to 10 parts by weight, in particular 4–7 parts by weight, of the curing catalyst (c).

In the mixtures according to the invention, the epoxide resin (a) employed can, in principle, be any type of epoxide resin, for example those having at least two glycidyl or β-methylglycidyl groups directly attached to an oxygen, nitrogen or sulfur atom or atoms. Examples of such epoxide resins which may be mentioned are the polyglycidyl and poly-(β-methylglycidyl)esters which can be obtained by reacting a compound containing two or more carboxylic acid groups per molecule with epichlorohydrin, glycerol dichlorohydrin or β-methylepichlorohydrin in the presence of an alkali. Polyglycidyl esters of this type can be derived from aliphatic polycarboxylic acids, for example succinic acid, glutaric acid, adipic acid, azelaic acid, sebacic acid or dimerised or trimerised linoleic acid, from cycloaliphatic polycarboxylic acids, such as tetrahydrophthalic acid, 4-methyltetrahydrophthalic acid, hexahydrophthalic acid and 4-methylhexahydrophthalic acid, and from aromatic polycarboxylic acids, such as phthalic acid, isophthalic acid and terephthalic acid.

Further examples are polyglycidyl and poly-(β-methylglycidyl)ethers, which can be obtained by reacting a compound containing at least two free alcoholic and/or phenolic hydroxyl groups per molecule with the corresponding epichlorohydrin under alkaline conditions, or in the presence of an acid catalyst with subsequent alkali treatment. These ethers can be prepared from acyclic alcohols, such as ethylene glycol, diethylene glycol and higher poly-(oxyethylene)glycols, propane-1,2-diol and poly-(oxypropylene)glycols, propane-1,3-diol, butane-1,4-diol, hexane-1,6-diol, hexane-2,4,6-triol, glycerol, 1,1,1-trimethylolpropane, pentaerythritol, sorbitol and polyepichlorohydrins, from cycloaliphatic alcohols, such as resorcitol, quinitol, bis-(4-hydroxycyclohexyl)-methane, 2,2-bis-(4-hydroxycyclohexyl)-propane and 1,1-bis-(hydroxymethyl)-3-cyclohexane, and from alcohols having aromatic nuclei, such as N,N-bis-(2-hydroxyethyl)-aniline and p,p'-bis-(2-hydroxyethylamino)-diphenylmethane. They can also be prepared from mononuclear phenols, such as resorcinol and hydroquinone, and polynuclear phenols, such as bis-(4-hydroxyphenyl)-methane, 4,4'-dihydroxybiphenyl, bis-(4-hydroxyphenyl)sulfone, 1,1,2,2-tetrakis-(4-hydroxyphenyl)-ethane, 2,2-bis-(4-hydroxyphenyl)-propane and 2,2-bis-(3,5-dibromo-4-hydroxyphenyl)-propane, and from novolaks which are formed from aldehydes, such as formaldehyde, acetaldehyde, chloral and furfural, by means of phenols, such as phenol itself and a phenol which is substituted in the ring by chlorine atoms or alkyl groups having in each case up to 9 carbon atoms, such as 4-chlorophenol, 2-methylphenol and 4-tert.-butylphenol.

Poly-(N-glycidyl) compounds embrace, for example, those which are obtained by dehydrochlorination of the reaction products of epichlorohydrin with amines containing at least two aminohydrogen atoms, such as aniline, n-butylamine, bis-(4-aminophenyl)-methane, m-xylylenediamine and bis-(4-methylaminophenyl)-methane, triglycidyl isocyanurate and N,N'-diglycidyl derivatives of cyclic alkyleneureas, such as ethyleneurea and 1,3-propyleneurea, and hydantoins, such as 5,5-dimethylhydantoin.

Examples of poly-(S-glycidyl) compounds are the di-S-glycidyl derivatives of dithiols, such as ethane-1,2-di-thiol and bis-(4-mercaptomethylphenyl)ether.

Further examples of suitable epoxide resins are also those in which the glycidyl groups are attached to heteroatoms of different kinds, for example the N,N,O-triglycidyl derivative of 4-aminophenol, the glycidyl ether/glycidyl ester of salicylic acid, N-glycidyl-N'-(2-glycidyloxypropyl)-5,5-dimethylhydantoin and 2-glycidyloxy-1,3-bis-(5,5-di-methyl-1-glycidylhydantoin-3-yl)-propane.

The cycloaliphatic epoxide resins in which the epoxy group is part of the aliphatic ring system, for example bis-(2,3-epoxycyclopentyl)ether, 2,3-epoxycyclopentyl glycidyl ether and 1,2-bis-(2,3-epoxycyclopentoxy)-ethane, are also suitable for the heat-curable mixtures according to the invention, but they are less suitable.

If desired, a mixture of epoxide resins can be used.

Preferred epoxide resins are polyglycidyl ethers and poly-(N-glycidyl) derivatives of aromatic amines. Particularly preferred resins are the polyglycidyl ethers of polynuclear phenols, such as 2,2-bis-(4-hydroxyphenyl)-propane, bis-(4-hydroxyphenyl)-methane or a novolak which has been formed from formaldehyde and phenol or phenol substituted in the ring of a chlorine atom or an alkyl having 1 to 4 C atoms, and which has a 1,2-epoxide content of at least 0.5 equivalent per kilogram.

Examples of imides (b) of the formula I which can be present in the mixtures according to the invention are allylbicyclo[2.2.1]hept-5-ene-2,3-dicarboximide, N-methyl-allylbicyclo[2.2.1]hept-5-ene-2,3-dicarboximide, N-allyl-allylbicyclo[2.2.1]hept-5-ene-2,3-dicarboximide, N-(2-ethylhexyl)-allylbicyclo[2.2.1]hept-5-ene-2,3-dicarboximide, N-cyclohexyl-allylbicyclo[2.2.1]hept-5-ene-2,3-dicarboximide, N-phenyl-allylbicyclo[2.2.1]hept-5-ene 2,3-dicarboximide, N-benzyl-allylbicyclo[2.2.1]hept-5-ene-2,3-dicarboximide, N,N'-ethylene-bis-(allylbicyclo[2.2.1]hept-5-ene-2,3-dicarboximide), N,N'-hexamethylene-bis-(allylbicyclo[2.2.1]hept-5-ene-2,3-dicarboximide), N,N'-dodecamethylene-bis-(allylbicyclo[2.2.1]hept-5-ene-2,3-dicarboximide), bis-[4-(allylbicyclo[2.2.1]hept-5-ene-dicarboximidophenyl)-methane], bis-[4-(methallylbicyclo[2.2.1]hept-5-ene-2,3-dicarboximidophenyl)-methane], N,N'-phenylene-bis-(allylbicyclo[2.2.1]hept-5-ene-2,3-dicarboximide), bis-[4-(allylbicyclo[2.2.1]hept-5-ene-2,3-dicarboximidophenyl)ether] and bis-[4-(allylbicyclo[2.2.1]hept-5-ene-2,3-dicarboximidophenyl)sulfone].

Imides (b) which are preferably employed in the mixtures according to the invention are those of the formula I in which E is allyl and G is hydrogen and, if n is 1, R is hydrogen, alkyl having 1-8 C atoms, allyl, cyclohexyl, phenyl hydroxyphenyl or benzyl, or, if n is 2, R is —(CH$_2$)$_m$— in which m is 2-12, m-phenylene or p-phenylene or a group of the formula II in which T is the methylene group, O or SO$_2$.

Compounds of the formula I which are particularly preferred are those in which E is the allyl group, G is hydrogen, n is the number 2 and R is —(CH$_2$)$_2$—, —(CH$_2$)$_6$— or

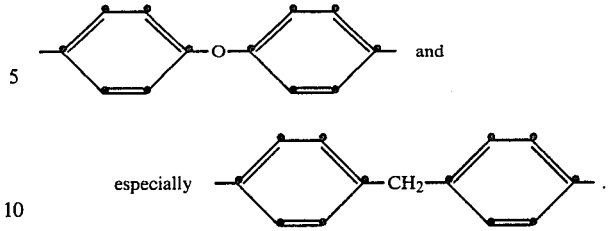

and especially 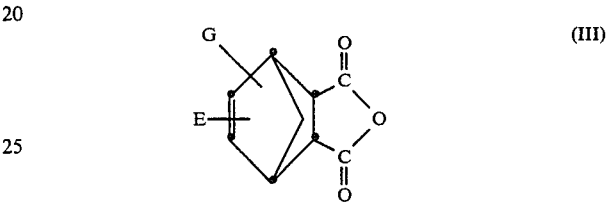

If desired, it is also possible to use a mixture of imides of the formula I.

The imides (b) which are present in the mixtures according to the invention can be prepared in a known manner by reacting, at an elevated temperature and with removal by distillation of the water formed in the reaction, an anhydride of the formula III

(III)

with a monoamine or diamine of the formula IV $(H_2N)_{\overline{n}}R$ (IV)

in which E, G, R and n are as defined under formula I.

If the compounds of the formula IV are ammonia or low-boiling monoamines, an excess of these reactants is advisable. Diamines should advantageously be employed in a stoichiometric ratio. The reaction can be carried out without a solvent or in the presence of an inert solvent (entraining agent) which can be used for the azeotropic removal of the water. The temperature of the reaction can be between 100° and 250° C. It is preferable to prepare the imides of the formula I in the melt under a pressure of not more than 4500 Pa and at temperatures between 130° and 220° C., in particular 180° and 220° C.

The anhydrides of the formula III can be prepared in accordance with the process described in U.S. Pat. No. 3,105,839 by reacting sodium cyclopentadienide with an allyl or methallyl halide, followed by a Diels-Alder reaction with maleic anhydride. Although it is indicated in the U.S. patent specification that the allyl group is attached in the 7-position of the bicyclic system, recent investigations show that a mixture is formed which is isomeric in respect of the position of the allyl group and also of the endo- and exo-configuration of the anhydride moiety. The isomeric components can only be separated by preparative gas chromatography.

Curing catalysts (c) which are suitable for the mixtures according to the invention are the customary catalysts which can be used for curing epoxide resins, for example imidazole and derivatives thereof substituted by alkyl, alkenyl, phenyl or benzyl, such as 1-methylimidazole, 2-ethyl-4-methylimidazole, 2-vinylimidazole, 2-phenylimidazole or 2-phenyl-4-methylimidazole, 1-(3-aminopropyl)-imidazole, N-acyl-substituted imidazoles, for example 1-(2,4,6-trimethylbenzoyl)-2-phenylimidazole, 1-(2,6-dichlorobenzoyl)-2-methylimidazole, 1-(2,6-dichlorobenzoyl)- phenylimidazole, 1-(2,6-dichlorobenzoyl)-2-ethyl-4-methylimidazole, 1-(2,6-dichlorobenzoyl)-4-phenylimidazole, 1-(2-chloro-6-nitrobenzoyl)-2-phenylimidazole, 1-(2-chloro-6-nitrobenzoyl)-2-ethylimidazole, 1-pentachlorobenzoyl-2-methylimidazole or 1-pentachlorobenzoyl-2-phenylimidazole, 1-propenyl-2-phenylimidazole or 1-propenyl-4-phenylimidazole, which are disclosed, for example, in German Offenlegungsschrift No. 3,246,072 and in Japanese Pat. No. 743,212, tertiary amines, such as diethylaminopropylamine, dimethylaminopropylamine, diethylaminoethylamine, dimethylaminobenzylamine or 1,6-bis-(dimethylamino)-hexane, and addition products formed from dimethylaminoalkylamines and glycidyl ethers of aliphatic alcohols or phenols. Such addition products preferably have the formula V

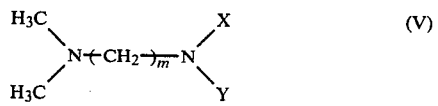

in which m is a number from 3 to 10, X is a grouping of the formula

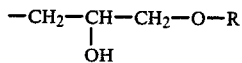

in which R is alkyl having 4 to 10 C atoms or phenyl which is unsubstituted or substituted by chlorine, bromine or alkyl or alkoxy having in each case 1 to 3 C atoms, and Y is a hydrogen atom or is as defined for X. Addition products of the formula indicated above are described, for example, in British Patent Specification No. 1,169,990 and in U.S. Pat. No. 3,332,997.

Further examples of compounds which can be used as curing catalysts are those of the formulae

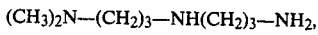

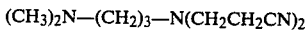

and also piperazine, dicyanodiamide, the known BF₃ complex compounds, for example the boron trifluoride/monethylamine complex, adducts formed from 1 mole of 1-(3-aminopropyl)-imidazole and 1 or 2 moles of glycidyl ethers of aliphatic alcohols or phenols, or adducts formed from 1 mole of 2-ethyl-4-methylimidazole, 2-methylimidazole or imidazole and 1 mole of a glycidyl ether of aliphatic alcohols or of a phenol. These adducts can also be prepared by the process described in British Patent Specification No. 1,169,990.

It is preferable to use, as the curing catalyst, imidazole and substituted derivatives thereof, especially the N-acyl-substituted imidazoles.

The mixtures according to the invention offer the advantage that they can be processed without a solvent. They have an advantageous processability, because they have a relatively low viscosity and have a good latency at processing temperatures up to 100° C. Above 100° C., the mixtures according to the invention then gel rapidly.

The mixtures according to the invention can be used for many purposes and are suitable, for example, for use as casting resins, laminating or impregnating resins, moulding materials, sealing materials, embedding and insulating materials for electrical engineering and, preferably, as adhesives and as matrix resins for composite materials, in particular for the production of fibre-reinforced plastics.

If desired, especially when modifying agents are concomitantly used, the mixtures according to the invention can be dissolved in an organic solvent, such as toluene, xylene, methyl ethyl ketone, methylene chloride, ethylene glycol monoalkyl and dialkyl ethers having 1-4 C atoms in the alkyl group(s) or a similar solvent, customary in the surface coating industry. Such solutions are suitable, in particular, for use as impregnating agents or coating agents.

It is also possible to add customary modifying agents, such as extenders, fillers and reinforcing agents, pigments, dyes, organic solvents, plasticisers, flow control agents, thixotropic agents, flame-retarding substances or mould release agents, to the curable mixtures according to the invention, before the latter are cured and in any phase. The following may be mentioned as examples of extenders, reinforcing agents, fillers and pigments which can be employed in the curable mixtures according to the invention: glass fibres, asbestos fibres, boron fibres, carbon fibres, fibres formed from aromatic polyamides, powdered quartz, mineral silicates, such as mica, powdered asbestos, powdered slate, kaolin, aluminium oxide, powdered chalk, antimony trioxide, Bentone, silica aerogel, lithopone, barytes, titanium dioxide, carbon black, graphite, oxide colorants, such as iron oxide, or metal powders, such as aluminium powder or iron powder, in particular the addition of 2-10% by weight of superfine Al₂O₃ or silica aerogel.

Examples of flow control agents which can be added when the curable mixtures are employed, particularly for the protection of surfaces, are silicones, liquid acrylic resins, cellulose acetobutyrate, polyvinylbutyral, waxes, stearates etc. (and these are also used to some extent as mould release agents).

Modifying agents which can be added to the curable mixtures in order to increase their flexibility and fracture toughness are polymers or prepolymers, such as polysulfone, polyamides, polyether-sulfones, polycarbonates or polyamideimide copolymers.

The mixtures according to the invention are preferably cured by heating them to a temperature within the range from 120° to 250° C., in particular 180° to 220° C. The curing can also be carried out in two or more stages in a known manner, the first curing stage being carried out at a low temperature and the subsequent curing at a higher temperature.

The present invention also relates, therefore, to the moulded materials, coatings and adhesive bonds obtained by curing from the curable mixtures according to the invention. In general, the moulded materials according to the invention are distinguished by relatively high glass transition temperatures, while having at the same time high mechanical strength values and high stability to moisture, and are especially distinguished by excellent resistance to prolonged heating and are therefore particularly suitable for the production of prepregs and high-grade composite materials.

The examples which follow illustrate the invention in greater detail. The imides (b) of the formula I used in the examples are prepared as follows:

Imide A

N,N'-Hexamethylene-bis-(allylbicyclo[2.2.1]hept-5-ene-2,3-dicarboximide)

A mixture of 204 g of allylbicyclo[2.2.1]hept-5-ene-2,3-dicarboxylic anhydride and 58 g of hexamethylenediamine is heated at 165° C. for 3 hours under a descending condenser and with stirring. The pressure is then reduced to 1866 Pa, and the mixture is stirred for a further hour at 175° C. This gives 235 g of an amber-coloured resin which is still just liquid at room temperature.

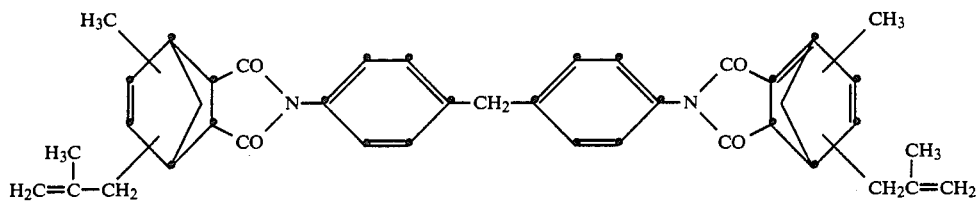

| Analysis: | % C | % H | % N |
|---|---|---|---|
| calculated for $C_{30}H_{36}N_2O_4$: | 73.74 | 7.43 | 5.73 |
| found: | 73.4 | 7.4 | 5.5 |

Imide B

N,N'-Ethylenebis-(allylbicyclo[2.2.1]hept-5-ene-2,3-dicarboximide)

204 g of allylbicyclo[2.2.1]hept-5-ene-2,3-dicarboxylic anhydride are initially taken and 30 g of ethylenediamine are added dropwise, with stirring. The temperature rises to 130° C. The temperature is increased to 180° C.; in the course of this 14 ml of water distil off. Heating is then continued for a further 2 hours at 200° C. and under a pressure of 9.3 Pa. This gives 210 g of a yellow resin, solid at room temperature and having a softening point of 56° C., measured on a Kofler heated stage.

| Analysis: | % C | % H | % N |
|---|---|---|---|
| calculated for $C_{26}H_{28}N_2O_4$: | 72.20 | 6.53 | 6.48 |
| found: | 71.7 | 6.5 | 6.4. |

Imide C

Bis-[4-(allylbicyclo[2.2.1]hept-5-ene-2,3-dicarboximidophenyl)]-methane

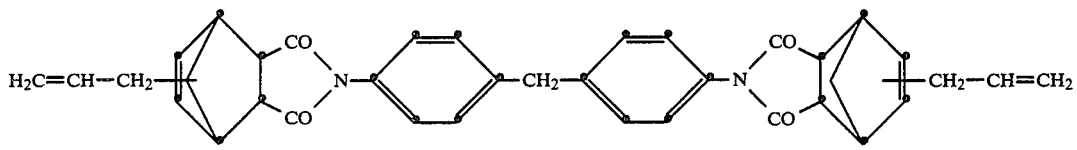

204 g of allylbicyclo[2.2.1]hept-5-ene-2,3-dicarboxylic anhydride and 99 g of 4,4'-diaminophenylmethane are heated in vacuo to 200° C. and are kept at this temperature for 1 hour. This gives 280 g of a brown solid resin having a softening point of 104° C., a viscosity of 0.425 Pa.s at 200° C. and an acid number of 0.

| Analysis: | % C | % H | % N |
|---|---|---|---|
| calculated for $C_{37}H_{34}N_2O_4$: | 77.87 | 6.01 | 4.91 |
| found: | 78.2 | 6.1 | 5.0 |

The following compounds are employed as curing catalysts in the examples:

Imide D

Bis-[4-(methallylmethylbicyclo[2.2.1]hept-5-ene-2,3-dicarboximidophenyl)]-methane

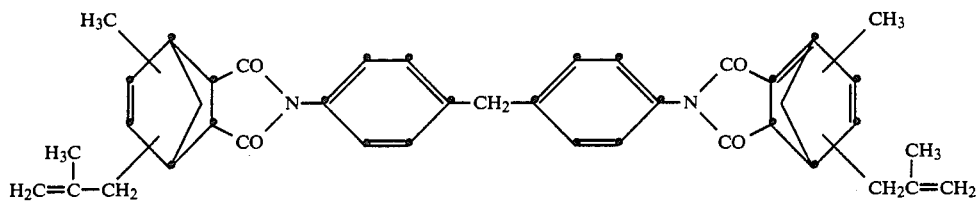

116 g of methallylmethylbicyclo[2.2.1]hept-5-ene-2,3-dicarboxylic anhydride and 49.5 g of 4,4'-diaminodiphenylmethane are heated to 200° C. in an $N_2$ atmosphere with stirring. 9 cm³ of water distill off. The glass transition temperature rises from 67.5° to 78.5° C. in the course of 35 minutes at 200° C. Yield: 155 g (99% of theory).

| Analysis: | calculated: | found: |
|---|---|---|
| % C | 78.57 | 77.41 |
| % H | 6.75 | 6.71 |
| % N | 4.47 | 4.38 |

Imide E

N-(4'-Hydroxyphenyl)-allylbicyclo[2.2.1]hept-5-ene-2,3-dicarboximide

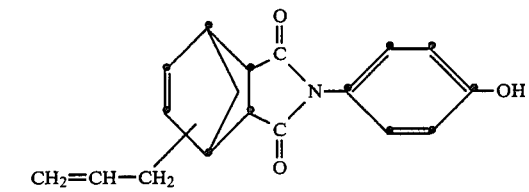

408 g of a mixture of isomers of allylbicyclo[2.2.1]hept-5-ene-2,3-dicarboxylic anhydride are heated with 238.26 g of 4-aminophenol to 200° C., the pressure is reduced to 2.7 Pa and the mixture is kept for 1 hour under these conditions. This gives 535 g of a red solid resin (87.7% of theory) having a glass transition temperature of 58° C.

| Analysis: | calculated: | found: |
|---|---|---|
| % C | 73.20 | 72.43 |

-continued

| Analysis: | calculated: | found: |
|---|---|---|
| % H | 5.90 | 6.05 |
| % N | 4.89 | 4.90 |
| % OH | 5.76 | 5.38 |

Catalyst I 1-(2,4,6-Trimethylbenzoyl)-2-phenylimidazole, which is prepared as follows:

144.2 g (1.00 mole) of 2-phenylimidazole are dissolved at 90° C. in 900 ml of toluene. 104.2 g (1.03 moles) of triethylamine are added to this solution, and a solution of 182.6 g (1.00 mole) of 2,4,6-trimethylbenzoyl chloride in 300 ml of toluene is added dropwise at 90° C. in the course of 2 hours, triethylamine hydrochloride being precipitated. The latter is filtered off with suction at room temperature and extracted by washing with toluene. Concentrating the filtrate gives 296 g of crude product, recrystallisation of which from 580 ml of acetonitrile gives a total of 227.3 g of 1-(2,4,6-trimethylbenzoyl)-2-phenylimidazole (78.3% of theory).

Catalyst II 1-(2,4,6-Trimethylbenzoyl)-2-ethylimidazole, which is prepared analogously to catalyst I using 2-ethylimidazole instead of 2-phenylimidazole.

Catalyst III 1-(2,6-Dichlorobenzoyl)-2-ethylimidazole, prepared from 2-ethylimidazole and 2,6-dichlorobenzoyl chloride analogously to catalyst I.

Catalyst IV 1-(2,6-Dichlorobenzoyl)-2-phenylimidazole, prepared from 2-phenylimidazole and 2,6-dichlorobenzoyl chloride analogously to catalyst I.

Catalyst V

2-Ethyl-4-methylimidazole

EXAMPLE 1

35 g of an epoxide-phenol novolak resin having an epoxide content of 5.6–5.8 equivalents/kg are heated to 100° C. and thoroughly mixed with 15 g of imide A and 2.1 g of catalyst I. The mixture has a viscosity of 48 mPa.s at 120° C. and a gel time of 116 minutes. After the mixture has been deaerated and cured in an aluminium (Anticorodal) mould 4 mm thick for 2 hours at 150° C. and for 2 hours at 250° C., homogeneous mouldings having the following properties are obtained:

Glass transition temperature Tg (measured using TMA 3000*) as the peak maximum of the penetration rate)=174° C.

*TMA 3000=thermomechanical analyser 3000 made by Mettler AG, Greifensee, Switzerland.

Flexural strength as specified in ISO 178 (FS) at 23° C.=120 mPa

Flexural strength as specified in ISO 178 after being kept for 10 days in $H_2O$ at 85° C.=104 mPa Edge elongation as specified in ISO 178 (EE)=6.3%

Fracture toughness (FT) (measured by the double torsion test)=111 $J/m^2$

Decomposition temperature (Td) (maximum vaporisation rate of the volatile fragments on warming at 4° C./minute)=417° C.

In order to determine the fracture toughness by the double torsion test in accordance with the instructions of P. W. R. Beaumont and R. J. Young, described in "Journal of Materials Science", 10, 1334 (1975) and 11, 776 (1979), two aluminium sections are glued by means of the curable mixture, and the adhesive bond is cured as indicated above. The crack propagation in the adhesive bond is measured in this method of measurement, i.e. the energy at break in $J/m^2$ is calculated from the maximum load for the crack propagation.

EXAMPLE 2

The following properties are determined by using 15 g of imide B and a composition and processing conditions otherwise the same as in Example 1:

Viscosity at 120° C. 77 mPa.s

Gel time at 120° C. 86 minutes

Tg 192° C.

FS 107 mPa

FS after being kept for 10 days in $H_2O$ at 85° C. 102 mPa

EE 5.0%

Torsional adhesive strength (twist-o-meter) (TS) at 25° C. 102 mPa

Torsional adhesive strength (twist-o-meter) (TS) at 120° C. 63 mPa

FT 70 $J/m^2$

The torsional adhesive strength is determined by gluing aluminium pegs in accordance with the instructions for measurements using the "twist-o-meter" (made by Epprecht, Instruments & Controls, Bassersdorf, Switzerland). This is effected by heating the curable mixture at 120° C. with stirring until a homogeneous solution of low viscosity is obtained. 5 adhesive bonds are prepared using the solution after it has been cooled to room temperature, and these bonds are then cured by heating for 2 hours at 150° C. and for 2 hours at 250° C.

EXAMPLE 3

Homogeneous mouldings having the following properties are obtained by using 15 g of imide C and processing and curing conditions otherwise the same as in Example 1:

Tg 212° C.

FS 105 mPa

FS after being kept for 10 days in $H_2O$ at 85° C. 99 mPa

EE 5.3%

TS at 250° C. 104 mPa

TS at 120° C. 63 mPa

EXAMPLE 4

30 g of imide A, 20 g of the epoxide-phenol novolak used in Example 1 and 1.2 g of catalyst I are used, curing is carried out for 2 hours at 150° C. and for 2 hours at 250° C., and the following properties are determined on the curable mixture or on the resulting mouldings:

Viscosity at 120° C 110 mPa.s

Gel time at 120° C. 700 minutes

Tg 172° C.

FS 110 mPa

EE 5.4%

TS at 25° C. 109 mPa

TS at 120° C. 68 mPa

EXAMPLE 5

The following properties are determined by using 50 g of epoxide-phenol novolak according to Example 1, 35 g of imide A and 15 g of imide C and 3 g of catalyst I, the processing and curing being otherwise the same as in Example 4:
Gel time at 120° C. 120 minutes
Tg 175° C.
FS 122 mPa
EE 6.0%
TS at 25° C. 118 mPa
TS at 120° C. 78 mPa
FT 78 J/m²

EXAMPLE 6

The moulded materials prepared from the following 3 mixtures are subjected to an ageing test:
(1) 50 g of epoxide-phenol novolak acccording to Example 1 +50 g of imide A
(2) 50 g of epoxide-phenol novolak according to Example 1 +50 g of imide C
(3) 50 g of epoxide-phenol novolak according to Example 1 +25 g of imide C+25 g of imide A 3 g of catalyst I are mixed with each of the mixtures. Curing procedure for the mixtures: 2 hours at 150° C. and 2 hours at 250° C.

After curing, the following values are determined on the mouldings:

|  | (1) | (2) | (3) |
|---|---|---|---|
| FS [mPa] | 110 | 117 | 113 |
| Elongation at break ($\epsilon$) [%] | 4.7 | 5.8 | 4.9 |
| the following changes in weight [%] are measured after the mouldings have been kept in water at 85° C. for 10 days: | | | |
|  | 1.90 | 2.05 | 2.00 |
| the following values are obtained after the mouldings have been kept in air at 160° C. for 10 days: | | | |
| FS [mPa] | 111 | 106 | 113 |
| $\epsilon$ [%] | 4.2 | 5.3 | 5.3 |
| the following values are obtained after the mouldings have been kept in air at 210° C. for 10 days: | | | |
| FS [mPa] | 85 | 88 | 101 |
| $\epsilon$ [%] | 2.9 | 3.2 | 3.8 |

The moulded materials obtained from the mixtures according to the invention are not very sensitive to moisture and have good stability when aged in hot air.

EXAMPLE 7

14 g of the epoxide resin according to Example 1 are mixed with 6 g of imide C under hot conditions; the mixture is then cooled to about 100° C. and mixed with 0.84 g of catalyst II. The mixture has a gel time of 8.4 minutes at 160° C. and, after being cured for 2 hours at 150° C. and 2 hours at 250° C., has a Tg of 170° C.

EXAMPLE 8

14 g of bisphenol A diglycidyl ether having an epoxide equivalent weight of 185, 6 g of imide C and 0.84 g of catalyst III are mixed and cured as in Example 7. The mixture has a gel time of 17.5 minutes at 160° C. The Tg of the cured mixture is 179° C.

EXAMPLE 9

14 g of N,N,N',N'-tetraglycidyldiaminodiphenylmethane are mixed with 6 g of imide A under hot conditions and, after cooling to about 100° C., are mixed with 0.84 g of catalyst IV. The mixture has a gel time of 37.5 minutes at 160° C. After curing in accordance with Example 7, the Tg of the moulding is 206° C.

EXAMPLE 10

14 g of an epoxide-phenol novolak having an epoxide solution weight of 191 and a functionality of about 3.5 epoxide groups per molecule are mixed with 6 g of imide A under hot conditions, and, after cooling to about 50° C., are mixed with 0.6 g of catalyst V. The mixture has a gel time of 1.2 minutes at 160° C. After the mixture has been cured in accordance with Example 7, the resulting moulding has a Tg of 184° C.

EXAMPLE 11

25 g of imide C, 25 g of imide A, 15 g of bisphenol A diglycidyl ether (BADG) having an epoxide equivalent weight of 185, 10 g of BADG having an epoxide equivalent weight of 413 and 25 g of an epoxide novolak according to Example 1 are mixed at a temperature of approx. 200° C. After the mixture has cooled to 100° C., 7 g of an adduct formed from 2 moles of phenyl glycidyl ether and 1 mole of dimethylaminopropylamine are mixed in, and processing and curing are carried out in accordance with Example 1. Mouldings having the following properties are obtained:
FS [mPa] 111
$\epsilon$ [%] 3.4.

EXAMPLE 12

60 g of epoxide resin according to Example 10 and 40 g of imide D are thoroughly mixed at approx. 200° C., cooled to 100° C. and mixed with 6 g of catalyst I. On processing and curing the mixture in accordance with Example 1 mouldings having the following properties are obtained:
Tg [°C.] 175
FS [mPa] 91.

EXAMPLE 13

15 g of imide E are thoroughly mixed at approx. 200° C. with 40 g of an epoxide novolak according to Example 1, 35 g of imide C and 10 g of an epoxide compound of the following structure:

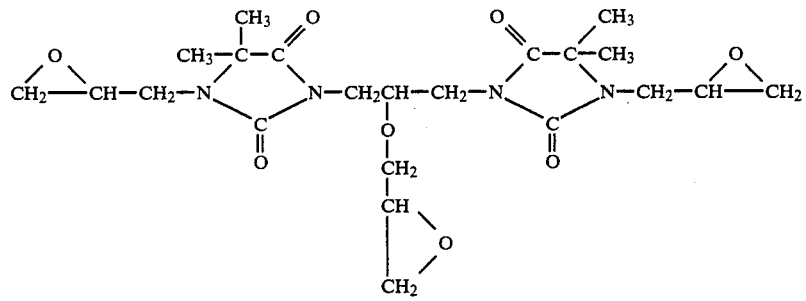

After the mixture has cooled to 80° C., 3 g of phenylimidazole are added. The mixture has a gel time of 7 minutes at 120° C. After it has been cured in accordance with Example 1, a moulding having a Tg of 199° C. is obtained.

EXAMPLE 14

50 g of epoxide compound according to Example 1 are mixed at approx. 200° C. with 50 g of imide E. After the mixture has cooled to 120° C., 2.25 g of catalyst I are added. After the mixture has been processed and cured in accordance with Example 1, mouldings having the following properties are obtained:

FS [mPa] 125
ε [%] 8.2.

What is claimed is:

1. A heat-curable mixture which is stable on storage and contains (a) 5 to 95 parts by weight of an epoxide resin having on average more than one epoxide group in the molecule, (b) 95 to 5 parts by weight of an allyl-substituted or methallyl-substituted imide of the formula I

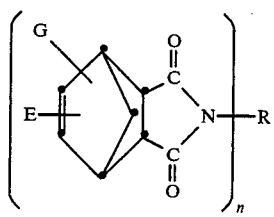

in which E is allyl or methallyl, G is hydrogen or methyl and n is 1 or 2 and, if n is 1, R is hydrogen, alkyl having 1–12 C atoms, alkenyl having 3–6 C atoms, cycloalkyl having 5–8 C atoms,
phenyl, tolyl, xylyl, hydroxyphenyl or naphthyl; or benzyl or, if n is 2, R is —$C_mH_{2m}$— in which m=2–20, m-phenylene, p-phenylene, 1,3-naphthylene, 1,4-naphthylene or 1,5-naphthylene or a group of the formula II

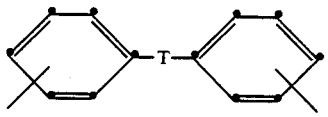

in which T is methylene, isopropylidene, CO, O, S or $SO_2$, and in which the total of (a) and (b) in the mixture is 100 parts by weight, and (c) 1 to 15 parts by weight, based on 100 parts by weight of the mixture of (a) and (b), of a curing catalyst.

2. A mixture according to claim 1, wherein G in formula I is hydrogen.

3. A mixture according to either of claims 1 or 2, which contains 20 to 70 parts by weight of the epoxide resin (a), 80 to 30 parts by weight of the imide (b) and 3 to 10 parts by weight of the catalyst (c).

4. A mixture according to either of claims 1 or 2, which contains, as the epoxide resin (a), a polyglycidyl ether or a poly-(N-glycidyl) derivative of an aromatic amine.

5. A mixture according to either of claims 1 or 2, which contains, as the epoxide resin (a), a polyglycidyl ether of a polynuclear phenol.

6. A mixture according to claim 1, which contains an imide of the formula I in which E is allyl and G is hydrogen and, if n is 1, R is hydrogen, alkyl having 1-8 C atoms, allyl, cyclohexyl, phenyl, hydroxyphenyl or benzyl, or, if n is 2, R is —$(CH_2)_m$— in which m is 2–12, m-phenylene or p-phenylene or a group of the formula II in which T is the methylene group, O or $SO_2$.

7. A mixture according to claim 1, which contains an imide of the formula I in which E is allyl, G is hydrogen, n is the number 2 and R is —$(CH_2)_2$—, —$(CH_2)_6$—,

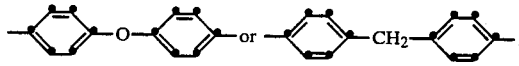

8. A mixture according to claim 1, which contains, as the catalyst (c), imidazole or substituted derivatives thereof.

9. A mixture according to claim 1, containing, as the catalyst (c), an N-acyl-substituted imidazole.

10. The moulded material, coating or adhesive bond obtained by curing from the curable mixture according to claim 1.

11. A mixture according to claim 7 wherein R is

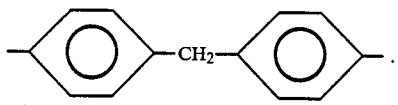

* * * * *